United States Patent
Zachar et al.

(10) Patent No.: US 10,286,170 B1
(45) Date of Patent: May 14, 2019

(54) CATHETER INFLATABLE CUFF PRESSURE STABILIZER

(71) Applicant: AIRWAY MEDIX S.A., Warsaw (PL)

(72) Inventors: Oron Zachar, Tel Aviv (IL); Yair Ramot, Kfar Maas (IL); Eizik Amar, Ashdod (IL)

(73) Assignee: AIRWAY MEDIX S.A., Warsaw (PL)

( * ) Notice: Subject to any disclaimer, the term of this patent is extended or adjusted under 35 U.S.C. 154(b) by 0 days.

(21) Appl. No.: 16/160,668

(22) Filed: Oct. 15, 2018

Related U.S. Application Data

(60) Provisional application No. 62/632,668, filed on Feb. 20, 2018.

(51) Int. Cl.
*A61M 16/04* (2006.01)
*A61M 25/10* (2013.01)

(52) U.S. Cl.
CPC ..... *A61M 16/044* (2013.01); *A61M 25/10182* (2013.11); *A61M 25/10184* (2013.11);
(Continued)

(58) Field of Classification Search
CPC .............. A61M 16/04; A61M 16/0434; A61M 16/044; A61M 16/045; A61M 16/0452;
(Continued)

(56) References Cited

U.S. PATENT DOCUMENTS 3,599,620 A * 8/1971 Balin ................ A61M 25/1018
604/920
3,782,363 A  1/1974 Davis
(Continued)

FOREIGN PATENT DOCUMENTS

WO  WO-2008038430 A1 * 4/2008 ............ A61M 16/04
WO  2011/133537 A1  10/2011
(Continued)

OTHER PUBLICATIONS

Alexandre Duguet, et al., "Control of tracheal cuff pressure: a pilot study using a pneumatic device," Intensive Care Med, Jan. 2007 (Oct. 25, 2006), pp. 128-132, vol. 33(1).
(Continued)

*Primary Examiner* — Jan Christopher L Merene
*Assistant Examiner* — Joseph D. Boecker
(74) *Attorney, Agent, or Firm* — Sughrue Mion, PLLC

(57) ABSTRACT

A cuff pressure stabilizer includes a substantially rigid protective housing and a balloon disposed therein. The balloon has a base low pressure of 10 cm H2O when it contains a base low-pressure volume of air. When the balloon contains a first medium-pressure volume of air, the balloon has a first medium pressure of 25 cm H2O, and less than 10% of an outer surface of the balloon touches an inner surface of the housing. When the balloon contains a second medium-pressure volume of air, the balloon has a second medium pressure of 40 cm H2O, and at least 20% of the outer surface of the balloon touches a portion of the inner surface of the housing. The second medium-pressure volume of air equals the base low-pressure volume of air plus a second incremental quantity of air that is between 10 cc and 60 cc. Other embodiments are also described.

26 Claims, 6 Drawing Sheets

(52) U.S. Cl.
CPC ............. *A61M 2025/1061* (2013.01); *A61M 2205/3341* (2013.01)

(58) Field of Classification Search
CPC .............. A61M 25/0155; A61M 25/10; A61M 25/1018; A61M 25/10181; A61M 25/10182; A61M 25/10183; A61M 25/10184; A61M 25/10188; A61M 2025/0018; A61M 2025/1059; A61M 2025/1061; A61M 2205/0216; A61M 2205/3341; A61B 2090/032
See application file for complete search history.

(56) References Cited

U.S. PATENT DOCUMENTS

| | | | |
|---|---|---|---|
| 3,794,043 A | 2/1974 | McGinnis | |
| 3,985,141 A | 10/1976 | Stanley et al. | |
| 4,016,885 A | 4/1977 | Bruner | |
| 4,064,882 A | 12/1977 | Johnson et al. | |
| 4,119,101 A * | 10/1978 | Igich | A61M 16/0486 128/202.16 |
| 4,134,407 A * | 1/1979 | Elam | A61M 16/04 116/270 |
| 4,135,494 A | 1/1979 | Stoner et al. | |
| 4,159,722 A | 7/1979 | Walker | |
| 4,182,344 A | 1/1980 | Benson | |
| 4,184,484 A | 1/1980 | Wright et al. | |
| 4,245,639 A | 1/1981 | La Rosa | |
| 4,501,273 A | 2/1985 | McGinnis | |
| 4,583,917 A | 4/1986 | Shah | |
| 4,598,707 A | 7/1986 | Agdanowski et al. | |
| 4,630,606 A | 12/1986 | Weerda et al. | |
| 4,649,914 A | 3/1987 | Kowalewski | |
| 4,988,342 A | 1/1991 | Herweck et al. | |
| 5,007,919 A * | 4/1991 | Silva | A61M 25/1018 604/121 |
| 5,098,384 A | 3/1992 | Abrams | |
| 5,218,970 A | 6/1993 | Turnbull et al. | |
| 5,255,670 A * | 10/1993 | Lomholt | A61M 16/044 128/200.24 |
| 5,279,601 A | 1/1994 | Lichte | |
| 5,361,753 A | 11/1994 | Pothmann et al. | |
| 5,487,383 A | 1/1996 | Levinson | |
| 6,439,232 B1 | 8/2002 | Brain | |
| 6,503,208 B1 | 1/2003 | Skovlund | |
| 6,647,984 B1 | 11/2003 | O'Dea | |
| 7,383,736 B2 | 6/2008 | Esnouf | |
| 8,291,768 B2 | 10/2012 | Spiegel et al. | |
| 8,397,577 B2 | 3/2013 | Slocum, Sr. et al. | |
| 2003/0037790 A1 | 2/2003 | Brain | |
| 2008/0078403 A1 | 4/2008 | Clayton | |
| 2009/0120445 A1* | 5/2009 | Chikashige | A61M 16/04 128/207.15 |
| 2011/0220116 A1 | 9/2011 | Lowenstein et al. | |
| 2011/0247412 A1 | 10/2011 | Scott | |
| 2011/0253145 A1 | 10/2011 | Calderoni et al. | |
| 2012/0090619 A1 | 4/2012 | Levine | |
| 2012/0204884 A1 | 8/2012 | Howard | |
| 2013/0014756 A1 | 1/2013 | Young et al. | |
| 2015/0283343 A1* | 10/2015 | Schnell | A61M 16/044 128/207.15 |
| 2015/0290410 A1* | 10/2015 | Schnell | A61M 16/044 128/207.15 |
| 2016/0158040 A1 | 6/2016 | Zupkofska | |

FOREIGN PATENT DOCUMENTS

| | | |
|---|---|---|
| WO | 2014/090680 A1 | 6/2014 |
| WO | 2017/153988 A1 | 9/2017 |

OTHER PUBLICATIONS

Christelle Lizy, et al., "Cuff Pressure of Endotracheal Tubes After Changes in Body Position in Critically ill Patients Treated With Mechanical Ventilation," American Journal of Critical Care, Jan. 2014, pp. e1-e8, vol. 23, No. 1.
Tracoe product catalogue excerpts 2016, 10 pgs.
Tracoe smart Cuff Manager, downloaded Feb. 15, 2018 from https://www.tracoe.com/en/products/technic/article/article/ref-730-5-tracoe-technic-smart-cuff-manager/, 3 pgs.
Tracoe smart cuff manager brochure Nov. 2017, 4 pgs.
Two-balloon experiment—Wikipedia downloaded Jan. 22, 2018, pp. 1-4.
International Search Report and Written Opinion for PCT/IL2017/050284 both dated Jun. 9, 2017 (PCT/ISA/210 and PCT/ISA237)).
An Office Action dated Feb. 27, 2018, which issued during the prosecution of U.S. Appl. No. 15/788,297.
An Office Action dated Jul. 11, 2018, which issued during the prosecution of U.S. Appl. No. 15/951,564.
An Office Action dated Jul. 6, 2018, which issued during the prosecution of U.S. Appl. No. 15/878,993.
An Office Action dated May 2, 2018, which issued during the prosecution of U.S. Appl. No. 15/878,993.
U.S. Appl. No. 62/632,668, filed Feb. 20, 2018.

* cited by examiner

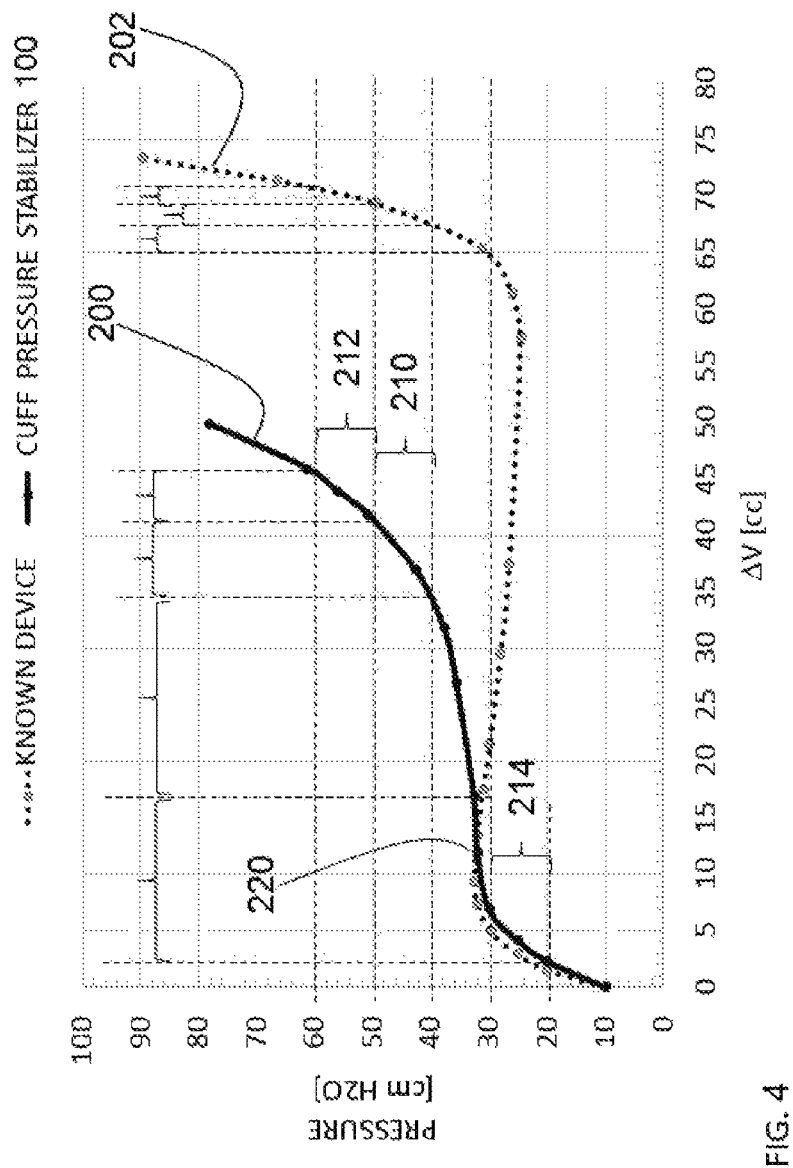

CATHETER INFLATABLE CUFF PRESSURE STABILIZER

CROSS-REFERENCE TO RELATED APPLICATIONS

The present application claims the benefit of U.S. Provisional Application 62/632,668, filed Feb. 20, 2018, which is assigned to the assignee of the present application and is incorporated herein by reference.

FIELD OF THE APPLICATION

The present invention relates generally to medical suction catheter systems, and specifically to airway ventilation device cuff systems.

BACKGROUND OF THE APPLICATION

Some endrotracheal tubes (ETTs) comprise an inflatable cuff, which forms a seal against the tracheal wall. This seal prevents gases from leaking past the cuff and allows positive pressure ventilation. Desired safe inflatable cuff pressure is in the range of 23-27 cm H2O, with an optimal pressure of about 25 cm H2O. Pressure above 30 cm H2O can cause irritation to the surrounding tracheal tissue. Extended duration of such high cuff pressure can interfere with oxygen flow to the tissue, causing tissue necrosis and a substantial wound. Low cuff pressure, typically below 20 cm H2O, compromises the cuff sealing performance, and allows leakage into the lungs of subglottic fluids descending from above the cuff.

The external surface of inflatable cuffs is in communication with the ventilation pressure of the lungs. The pressure of the inflatable cuff cycles with the ventilation cycle. When an artificially-ventilated patient is also anesthetized, the plastic of the inflatable cuff absorbs the nitrous oxide (N2O) gas used in anesthesia, which increases pressure in the cuff.

In current clinical settings of intensive care patients, changes of body positioning lead to significant changes in cuff pressure in the range of 10-50 cm H2O, i.e., out of the safe range of 20-30 cm H2O, and certainly out of the desired range of 23-27 cm H2O. See, for example, Lizy C et al., "Cuff pressure of endrotracheal tubes after changes in body position in critically ill patients treated with mechanical ventilation," Am J Crit Care. 2014 January; 23(1):e1-8.

Therefore, there is a need to safely maintain the inflatable cuff pressure is in the range of 23-27 cm H2O, optimally about 25 cm H2O, and to avoid extended periods of pressure above 30 cm H2O. In particular, there is a need to suppress the fluctuations of pressure in clinical settings caused by patient change of body positions.

Currently, the most common practiced approach for ETT cuff pressure management is manual monitoring (using a manometer) and adjustment of cuff pressure, which contributes to ICU staff workload. It has been shown that up to eight manual adjustments of cuff pressure are required daily to maintain recommended cuff pressure ranges. Even so, the cuff pressure is uncontrolled during the long time periods between manual cuff adjustments. In addition, the manometer must be connected to and disconnected from the ETT cuff for each pressure measurement, which allows a small amount of air to escape from the ETT cuff. Still further, many conventional ETT manometers lose calibration relatively quickly.

Prior art cuff pressure regulators can be divided into two groups: (a) large bedside non-disposable expensive electric pump and electronic pressure monitors: and (b) small and light disposable non-electric limited-pressure reservoir compartments that must be filled manually. Use of disposable devices both prevents cross-contamination between patients and obviates the need for costly sterilization processes between patients. Moreover, the compactness of the disposable devices allows them to be attached on the ETT circuit and not occupy bedside space and an electric power cable connection.

Laryngeal mask airway (LMA) devices are useful in facilitating lung ventilation by forming a low-pressure seal around the patient's laryngeal inlet, thereby avoiding the known harmful effects of ETT devices, which form a seal within the trachea. LMA devices have become standard medical devices, instead of ETT devices, for rapidly and reliably establishing an unobstructed airway in a patient in emergency situations and in the administration of anesthetic gases.

During general anesthesia, pulmonary ventilation is secured with an ETT device or by an LMA device, and attention to the risk of complications related to a high intracuff pressure is important. When the cuff-to-tracheal wall pressure exceeds the tracheal capillary pressure (130-140 cm H2O) for approximately 15 minutes, the tracheal mucous membrane becomes ischemic. The intracuff pressure approximates the cuff-to-tracheal wall pressures in high volume/low pressure cuffs, and a cuff pressure below 120 cm H2O is recommended to prevent ischemic injury. In addition, recurrent laryngeal nerve palsy has been demonstrated in up to 5% of patients after intubation, and a high cuff pressure is suspected as contributing to this complication. Similarly, in patients provided with a laryngeal mask, a high cuff pressure may lead to palsy of the lingual, hypoglossal, and recurrent laryngeal nerves, and postoperative sore throat.

US Patent Application Publication 2015/0283343 to Schnell et al. describes a pressure-equalizing device with a pressure equalizing balloon, the volume of which is connected to a further volume, the pressure of which is intended to be kept at as constant a value as possible even in the event of an enforced change in volume. In order therefore to keep the cuff pressure within the pressure range that is generally considered to be useful and optimal of between approximately 20 mbar and 30 mbar, but also make possible, if required, to increase the pressure in a controlled manner, according to the invention the equalizing balloon keeping the pressure generally constant is accommodated in a protective sleeve which has radial bulges deviating from a uniformly concave form matched to the outer contour of the balloon, which bulges are designed such that the equalizing balloon first abuts against the wall areas of the protective sleeve matched to the contour of the balloon and then, when pressure is increased, extends only into the bulges, whereby the pressure in the equalizing balloon gradually increases as the volume in the bulges increases.

PCT Publication WO 2017/153988 to Zachar et al., which is incorporated herein by reference, describes a cuff pressure stabilizer that includes an inflation lumen proximal port connector, which is shaped to form an air-tight seal with an inflation lumen proximal port of a catheter additionally having an inflatable cuff and an inflation lumen; a fluid reservoir; a liquid column container, which is (a) open to the atmosphere at at least one site along the liquid column container, (b) in fluid communication with the fluid reservoir, and (c) in communication with the inflation lumen proximal port connector via the fluid reservoir: and a liquid, which is contained (a) in the fluid reservoir, (b) in the liquid column container, or (c) partially in the fluid reservoir and partially in the liquid column container, and which has a density of between 1.5 and 5 g/cm3 at 4 degrees Celsius at 1 atm.

SUMMARY OF THE APPLICATION

Applications of the present invention provide a cuff pressure stabilizer for use with an airway ventilation device having an inflatable cuff. The same cuff pressure stabilizer, without requiring adjustment, calibration, or other configuration, is able to provide pressure stabilization to inflatable cuffs of both tracheal ventilation tubes and laryngeal mask airway (LMA) devices, even though the cuffs of these devices are inflated to substantially different pressures. Typically, cuffs of tracheal ventilation tubes are inflated to 25-30 cm H2O, while cuffs of LMA devices are inflated to 40-60 cm H2O. In order to provide this pressure stabilization over such a wide range of pressures, the cuff pressure stabilizer comprises an elastic balloon, which is in fluid communication with the inflatable cuff, and which is disposed inside a substantially rigid protective housing that is configured to provide a pressure-volume curve with certain characteristics.

Typically, the protective housing is shaped and an inflatable portion of the balloon is configured such that:
  when the inflatable portion of the balloon contains a base low-pressure volume of air, the inflatable portion of the balloon has a base low pressure of 10 cm H2O,
  when the inflatable portion of the balloon contains a first medium-pressure volume of air. (a) the inflatable portion of the balloon has a first medium pressure of 25 cm H2O. and (b) none of or less than 10% of an outer surface of the inflatable portion of the balloon touches an inner surface of the protective housing; the first medium-pressure volume of air equals the sum of (a) the base low-pressure volume of air and (b) a first incremental quantity of air of less than 10 cc, and
  when the inflatable portion of the balloon contains a second medium-pressure volume of air, (a) the inflatable portion of the balloon has a second medium pressure of 40 cm H2O, and (b) at least 20% of the outer surface of the inflatable portion of the balloon touches a portion of the inner surface of the protective housing; the second medium-pressure volume of air equals the sum of (a) the base low-pressure volume of air and (b) a second incremental quantity of air that is between 10 cc and 60 cc.

The inflatable portion of the balloon is characterized by a pressure-volume curve that represents the pressure in the inflatable portion of the balloon when inflated with different incremental volumes of air beyond the above-mentioned base low-pressure volume of air. The area of physical contact between the outer surface of the balloon and the inner surface of the protective housing at different pressures/volumes has a strong influence on the shape of the pressure-volume curve, because the contact affects the minimum radius of curvature of the balloon, and the pressure in a balloon is approximately proportional to the ratio of the surface tension to the minimum radius of curvature of the balloon. At a first stage, when the balloon is inflated at low pressure, its radius of curvature increases with increased inflation volume. In contrast, after contact with the shaped protective housing, the balloon's radius of curvature decreases upon further increased inflation volume, while the surface tension of the balloon continues to increase with inflation. The shape of the inner surface of the protective housing thus affects the shape of the pressure-volume curve of the balloon, including the presence and locations of local maximums and minimums and points of inflection.

For some applications, in order to provide the desired pressure-volume curve, the protective housing is shaped so as to define an inner surface that includes a frustoconical portion. The balloon is arranged such that (a) none or less than 10% of the outer surface of the inflatable portion of the balloon touches the frustoconical portion when the inflatable portion of the balloon is inflated to a first medium pressure of 25 cm H2O, and (b) at least 20% of the outer surface of the inflatable portion of the balloon touches at least a portion of the frustoconical portion when the inflatable portion of the balloon is inflated to a second medium pressure greater than the first medium pressure. Optionally, the inner surface of the protective housing includes two frustoconical portions.

During use of the cuff pressure stabilizer, a healthcare worker inflates the inflatable cuff of the airway ventilation device to an initial desired pressure. The cuff pressure stabilizer is configured to automatically mechanically and non-electrically stabilize the pressure in the inflatable cuff to within a clinically-acceptable range above and below the initial desired pressure, so long as the initial desired pressure is within the normal clinically-acceptable range for cuffs of tracheal ventilation tubes or LMA devices.

There is therefore provided, in accordance with an Inventive concept 1 of the present invention, a cuff pressure stabilizer for use with an airway ventilation device having an inflatable cuff, an inflation lumen, and an inflation lumen proximal port, the cuff pressure stabilizer including:
  a stabilizer port, which is configured to be coupled in fluid communication with the inflation lumen proximal port;
  a substantially rigid protective housing; and
  an elastic balloon, which is in fluid communication with the stabilizer port, and which is arranged such that an inflatable portion of the balloon is disposed inside the protective housing,
  wherein the protective housing is shaped and the inflatable portion of the balloon is configured such that:
    when the inflatable portion of the balloon contains a base low-pressure volume of air, the inflatable portion of the balloon has a base low pressure of 10 cm H2O,
    when the inflatable portion of the balloon contains a first medium-pressure volume of air, (a) the inflatable portion of the balloon has a first medium pressure of 25 cm H2O, and (b) none of or less than 10% of an outer surface of the inflatable portion of the balloon touches an inner surface of the protective housing, wherein the first medium-pressure volume of air equals the sum of (a) the base low-pressure volume of air and (b) a first incremental quantity of air of less than 10 cc, and
    when the inflatable portion of the balloon contains a second medium-pressure volume of air, (a) the inflatable portion of the balloon has a second medium pressure of 40 cm H2O, and (b) at least 20% of the outer surface of the inflatable portion of the balloon touches a portion of the inner surface of the protective housing, wherein the second medium-pressure volume of air equals the sum of (a) the base low-pressure volume of air and (b) a second incremental quantity of air that is between 10 cc and 60 cc.

Inventive concept 2. The cuff pressure stabilizer according to Inventive concept 1, wherein the second incremental quantity of air is less than 40 cc.

Inventive concept 3. The cuff pressure stabilizer according to Inventive concept 2, wherein the second incremental quantity of air is less than 30 cc.

Inventive concept 4. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air, and
wherein the pressure-volume curve does not include a local maximum pressure at any pressure between 20 and 50 cm H2O.

Inventive concept 5. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air,
wherein the pressure-volume curve includes a local maximum pressure and a local minimum pressure at a greater incremental volume than the local maximum pressure, and
wherein a pressure difference between the local maximum pressure and the local minimum pressure is less than 3 cm H2O.

Inventive concept 6. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air,
wherein the pressure-volume curve includes a local maximum pressure and a local minimum pressure at a greater incremental volume than the local maximum pressure, and
wherein a volume difference between the local maximum pressure and the local minimum pressure is less than 40 cc.

Inventive concept 7. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air, and
wherein an average rate of change of the pressure-volume curve over a pressure interval between 40 and 50 cm H2O is between 0.5 and 3 cm H2O/cc.

Inventive concept 8. The cuff pressure stabilizer according to Inventive concept 7, wherein the average rate of change of the pressure-volume curve over the pressure interval between 40 and 50 cm H2O is less than 2 cm H2O/cc.

Inventive concept 9. The cuff pressure stabilizer according to Inventive concept 8, wherein the average rate of change of the pressure-volume curve over the pressure interval between 40 and 50 cm H2O is less than 1 cm H2O/cc.

Inventive concept 10. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air, and
wherein an average rate of change of the pressure-volume curve over a pressure interval between 50 and 60 cm H2O is between 0.5 and 3 cm H2O/cc.

Inventive concept 11. The cuff pressure stabilizer according to Inventive concept 10, wherein the average rate of change of the pressure-volume curve over the pressure interval between 50 and 60 cm H2O is less than 2 cm H2O/cc.

Inventive concept 12. The cuff pressure stabilizer according to Inventive concept 11, wherein the average rate of change of the pressure-volume curve over the pressure interval between 50 and 60 cm H2O is less than 1 cm H2O/cc.

Inventive concept 13. The cuff pressure stabilizer according to Inventive concept 1,
wherein the inflatable portion of the balloon is characterized by a pressure-volume curve that represents the pressure in the inflatable portion of the balloon when inflated with different incremental volumes of air beyond the base low-pressure volume of air, and
wherein an average rate of change of the pressure-volume curve over a pressure interval between 20 and 30 cm H2O is between 1 and 5 cm H2O/cc.

Inventive concept 14. The cuff pressure stabilizer according to Inventive concept 13, wherein the average rate of change of the pressure-volume curve over the pressure interval between 20 and 30 cm H2O is less than 4 cm H2O/cc.

Inventive concept 15. The cuff pressure stabilizer according to Inventive concept 14, wherein the average rate of change of the pressure-volume curve over the pressure interval between 20 and 30 cm H2O is less than 3 cm H2O/cc.

Inventive concept 16. The cuff pressure stabilizer according to Inventive concept 1,
wherein the protective housing is shaped so as to define an inner surface that includes a frustoconical portion, and
wherein the protective housing is shaped and the inflatable portion of the balloon is configured such that:
when the inflatable portion of the balloon contains the first medium-pressure volume of air, none or less than 10% of the outer surface of the inflatable portion of the balloon touches the frustoconical portion, and
when the inflatable portion of the balloon contains the second medium-pressure volume of air, at least 20% of the outer surface of the inflatable portion of the balloon touches at least a portion of the frustoconical portion.

Inventive concept 17. The cuff pressure stabilizer according to Inventive concept 16, wherein the frustoconical portion of the inner surface of the protective housing that comes into contact with the balloon when the balloon is inflated to a medium pressure of 50 cm H2O has an area of between 10 and 60 cm2.

Inventive concept 18. The cuff pressure stabilizer according to Inventive concept 16, wherein the protective housing is shaped such that the frustoconical portion is part of a conical portion of the inner surface.

Inventive concept 19. The cuff pressure stabilizer according to Inventive concept 16, wherein the protective housing is cylindrically symmetric about a central longitudinal axis defined by the frustoconical portion.

Inventive concept 20. The cuff pressure stabilizer according to Inventive concept 16, wherein the frustoconical portion is a first frustoconical portion, and wherein the protective housing is shaped such that the inner surface includes a second frustoconical portion, and wherein the first and the second frustoconical portions geometrically define different respective apices.

Inventive concept 21. The cuff pressure stabilizer according to Inventive concept 20, wherein the first and the second frustoconical portions share a common central longitudinal axis.

Inventive concept 22. The cuff pressure stabilizer according to Inventive concept 20, wherein respective cones geometrically defined by the first and the second frustoconical portions intersect each other at one or more angles, at least one of which is greater than 45 degrees.

Inventive concept 23. The cuff pressure stabilizer according to Inventive concept 22, wherein at least one of the angles is less than 90 degrees.

Inventive concept 24. The cuff pressure stabilizer according to Inventive concept 22, wherein all of the angles are greater than 45 degrees.

Inventive concept 25. The cuff pressure stabilizer according to Inventive concept 22, wherein all of the angles are less than 90 degrees.

Inventive concept 26. The cuff pressure stabilizer according to Inventive concept 22, wherein the respective cones geometrically defined by the first and the second frustoconical portions intersect each other at exactly one angle.

Inventive concept 27. The cuff pressure stabilizer according to Inventive concept 20, wherein the balloon is arranged such that the inflatable portion of the balloon is disposed inside the protective housing such that as the inflatable portion of the balloon is inflated from the first medium pressure toward the second medium pressure, the outer surface of the inflatable portion of the balloon increases contact with the second frustoconical portion before increasing contact with the first frustoconical portion.

Inventive concept 28. The cuff pressure stabilizer according to Inventive concept 16, wherein the balloon is shaped so as to define an inflation inlet, and wherein a proximal surface of the protective housing is shaped so as to define an inflation opening aligned with the inflation inlet, such that the inflatable portion of the balloon is inflatable via the inflation opening of the protective housing, wherein the inner surface of the protective housing includes a proximal portion that faces generally distally, and a distal portion that faces generally proximally toward the proximal portion, and wherein one of the proximal and the distal portions of the inner surface includes the frustoconical portion.

Inventive concept 29. The cuff pressure stabilizer according to Inventive concept 28, wherein a cone geometrically defined by the frustoconical portion intersects the other one of the proximal and the distal portions of the inner surface at one or more angles, at least one of which is greater than 45 degrees.

Inventive concept 30. The cuff pressure stabilizer according to Inventive concept 28, wherein the other one of the proximal and the distal portions of the inner surface is generally flat.

Inventive concept 31. The cuff pressure stabilizer according to Inventive concept 30, wherein a cone geometrically defined by the frustoconical portion intersects the other one of the proximal and the distal portions of the inner surface at one or more angles, at least one of which is greater than 45 degrees.

Inventive concept 32. The cuff pressure stabilizer according to Inventive concept 28, wherein the frustoconical portion is a first frustoconical portion, and wherein the other one of the proximal and the distal portions of the inner surface defines a second frustoconical portion.

Inventive concept 33. The cuff pressure stabilizer according to Inventive concept 32, wherein respective cones geometrically defined by the first and the second frustoconical portions intersect each other at one or more angles, at least one of which is greater than 45 degrees.

Inventive concept 34. The cuff pressure stabilizer according to any one of Inventive concepts 1-33, further including:

a pressure sensor, which is configured to sense a pressure in the inflatable portion of the balloon; and a pressure display, which is configured to display the pressure sensed by the pressure sensor.

Inventive concept 35. The cuff pressure stabilizer according to Inventive concept 34, wherein the pressure display is digital.

Inventive concept 36. A system including the cuff pressure stabilizer according to any one of Inventive concepts 1-33, wherein the system further includes the airway management device.

Inventive concept 37. The system according to Inventive concept 36, wherein the airway management device includes a tracheal ventilation tube.

Inventive concept 38. The system according to Inventive concept 36, wherein the airway management device includes a laryngeal mask airway (LMA) device.

There is further provided, in accordance with an Inventive concept 39 of the present invention, a cuff pressure stabilizer for use with an airway ventilation device having an inflatable cuff, an inflation lumen, and an inflation lumen proximal port, the cuff pressure stabilizer including:

a stabilizer port, which is configured to be coupled in fluid communication with the inflation lumen proximal port;

a substantially rigid protective housing; and an elastic balloon, which is in fluid communication with the stabilizer port, and which is arranged such that an inflatable portion of the balloon is disposed inside the protective housing, wherein the protective housing is shaped and the inflatable portion of the balloon is configured such that:

when the inflatable portion of the balloon contains a base low-pressure volume of air, the inflatable portion of the balloon has a base low pressure of 10 cm H2O, the inflatable portion of the balloon is characterized by a pressure-volume curve that represents the pressure in the inflatable portion of the balloon when inflated with different incremental volumes of air beyond the base low-pressure volume of air, and the pressure-volume curve includes a rising point of inflection at a pressure of between 25 and 40 cm H2O.

Inventive concept 40. The cuff pressure stabilizer according to Inventive concept 39, wherein the pressure-volume curve does not include a local maximum pressure at any pressure between 20 and 50 cm H2O.

Inventive concept 41. The cuff pressure stabilizer according to Inventive concept 39, wherein an average rate of change of the pressure-volume curve over a pressure interval between 40 and 50 cm H2O is between 0.5 and 3 cm H2O/cc.

Inventive concept 42. The cuff pressure stabilizer according to Inventive concept 41, wherein the average rate of change of the pressure-volume curve over the pressure interval between 40 and 50 cm H2O is less than 2 cm H2O/cc.

Inventive concept 43. The cuff pressure stabilizer according to Inventive concept 42, wherein the average rate of change of the pressure-volume curve over the pressure interval between 40 and 50 cm H2O is less than 1 cm H2O/cc.

Inventive concept 44. The cuff pressure stabilizer according to Inventive concept 39, wherein an average rate of change of the pressure-volume curve over a pressure interval between 50 and 60 cm H2O is between 0.5 and 3 cm H2O/cc.

Inventive concept 45. The cuff pressure stabilizer according to Inventive concept 44, wherein the average rate of change of the pressure-volume curve over the pressure interval between 50 and 60 cm H2O is less than 2 cm H2O/cc.

Inventive concept 46. The cuff pressure stabilizer according to Inventive concept 45, wherein the average rate of change of the pressure-volume curve over the pressure interval between 50 and 60 cm H2O is less than 1 cm H2O/cc.

Inventive concept 47. The cuff pressure stabilizer according to Inventive concept 39, wherein an average rate of change of the pressure-volume curve over a pressure interval between 20 and 30 cm H2O is between 1 and 5 cm H2O/cc.

Inventive concept 48. The cuff pressure stabilizer according to Inventive concept 47, wherein the average rate of change of the pressure-volume curve over the pressure interval between 20 and 30 cm H2O is less than 4 cm H2O/cc.

Inventive concept 49. The cuff pressure stabilizer according to Inventive concept 48, wherein the average rate of change of the pressure-volume curve over the pressure interval between 20 and 30 cm H2O is less than 3 cm H2O/cc.

Inventive concept 50. The cuff pressure stabilizer according to any one of Inventive concepts 39-49, further including:
 a pressure sensor, which is configured to sense a pressure in the inflatable portion of the balloon; and
 a pressure display, which is configured to display the pressure sensed by the pressure sensor.

Inventive concept 51. The cuff pressure stabilizer according to Inventive concept 50, wherein the pressure display is digital.

Inventive concept 52. A system including the cuff pressure stabilizer according to any one of Inventive concepts 39-49, wherein the system further includes the airway management device.

Inventive concept 53. The system according to Inventive concept 52, wherein the airway management device includes a tracheal ventilation tube.

Inventive concept 54. The system according to Inventive concept 52, wherein the airway management device includes a laryngeal mask airway (LMA) device.

There is still further provided, in accordance with an Inventive concept 55 of the present invention, a cuff pressure stabilizer for use with an airway ventilation device having an inflatable cuff, an inflation lumen, and an inflation lumen proximal port, the cuff pressure stabilizer including:
 a stabilizer port, which is configured to be coupled in fluid communication with the inflation lumen proximal port;
 a substantially rigid protective housing, which is shaped so as to define an inner surface that includes a frustoconical portion; and
 an elastic balloon, which is in fluid communication with the stabilizer port, and which is arranged such that an inflatable portion of the balloon is disposed inside the protective housing, such that (a) none or less than 10% of an outer surface of the inflatable portion of the balloon touches the frustoconical portion when the inflatable portion of the balloon is inflated to a first medium pressure of 25 cm H2O, and (b) at least 20% of the outer surface of the inflatable portion of the balloon touches at least a portion of the frustoconical portion when the inflatable portion of the balloon is inflated to a second medium pressure greater than the first medium pressure.

Inventive concept 56. The cuff pressure stabilizer according to Inventive concept 55, wherein the frustoconical portion of the inner surface of the protective housing that comes into contact with the balloon when the balloon is inflated to a medium pressure of 50 cm H2O has an area of between 10 and 60 cm2.

Inventive concept 57. The cuff pressure stabilizer according to Inventive concept 55, wherein the protective housing is shaped such that the frustoconical portion is part of a conical portion of the inner surface.

Inventive concept 58. The cuff pressure stabilizer according to Inventive concept 55, wherein the protective housing is cylindrically symmetric about a central longitudinal axis defined by the frustoconical portion.

Inventive concept 59. The cuff pressure stabilizer according to Inventive concept 55, wherein the frustoconical portion is a first frustoconical portion, and wherein the protective housing is shaped such that the inner surface includes a second frustoconical portion, and wherein the first and the second frustoconical portions geometrically define different respective apices.

Inventive concept 60. The cuff pressure stabilizer according to Inventive concept 59, wherein the first and the second frustoconical portions share a common central longitudinal axis.

Inventive concept 61. The cuff pressure stabilizer according to Inventive concept 59, wherein respective cones geometrically defined by the first and the second frustoconical portions intersect each other at one or more angles, at least one of which is greater than 45 degrees.

Inventive concept 62. The cuff pressure stabilizer according to Inventive concept 61, wherein at least one of the angles is less than 90 degrees.

Inventive concept 63. The cuff pressure stabilizer according to Inventive concept 61, wherein all of the angles are greater than 45 degrees.

Inventive concept 64. The cuff pressure stabilizer according to Inventive concept 61, wherein all of the angles are less than 90 degrees.

Inventive concept 65. The cuff pressure stabilizer according to Inventive concept 61, wherein the respective cones geometrically defined by the first and the second frustoconical portions intersect each other at exactly one angle.

Inventive concept 66. The cuff pressure stabilizer according to Inventive concept 59, wherein the balloon is arranged such that the inflatable portion of the balloon is disposed inside the protective housing such that as the inflatable portion of the balloon is inflated from the first medium pressure toward the second medium pressure, the outer surface of the inflatable portion of the balloon increases contact with the second frustoconical portion before increasing contact with the first frustoconical portion.

Inventive concept 67. The cuff pressure stabilizer according to Inventive concept 55,
 wherein the balloon is shaped so as to define an inflation inlet, and wherein a proximal surface of the protective housing is shaped so as to define an inflation opening aligned with the inflation inlet, such that the inflatable portion of the balloon is inflatable via the inflation opening of the protective housing,
 wherein the inner surface of the protective housing includes a proximal portion that faces generally distally, and a distal portion that faces generally proximally toward the proximal portion, and
 wherein one of the proximal and the distal portions of the inner surface includes the frustoconical portion.

Inventive concept 68. The cuff pressure stabilizer according to Inventive concept 67, wherein a cone geometrically defined by the frustoconical portion intersects the other one of the proximal and the distal portions of the inner surface at one or more angles, at least one of which is greater than 45 degrees.

Inventive concept 69. The cuff pressure stabilizer according to Inventive concept 67, wherein the other one of the proximal and the distal portions of the inner surface is generally flat.

Inventive concept 70. The cuff pressure stabilizer according to Inventive concept 69, wherein a cone geometrically defined by the frustoconical portion intersects the other one of the proximal and the distal portions of the inner surface at one or more angles, at least one of which is greater than 45 degrees.

Inventive concept 71. The cuff pressure stabilizer according to Inventive concept 67, wherein the frustoconical portion is a first frustoconical portion, and wherein the other one of the proximal and the distal portions of the inner surface defines a second frustoconical portion.

Inventive concept 72. The cuff pressure stabilizer according to Inventive concept 71, wherein respective cones geometrically defined by the first and the second frustoconical portions intersect each other at one or more angles, at least one of which is greater than 45 degrees.

Inventive concept 73. A system including the cuff pressure stabilizer according to any one of Inventive concepts 55-72, wherein the system further includes the airway management device.

Inventive concept 74. The system according to Inventive concept 73, wherein the airway management device includes a tracheal ventilation tube.

Inventive concept 75. The system according to Inventive concept 73, wherein the airway management device includes a laryngeal mask airway (LMA) device.

There is additionally provided, in accordance with an Inventive concept 76 of the present invention, a method for use with an airway ventilation device having an inflatable cuff, an inflation lumen, and an inflation lumen proximal port, the method including:

providing a cuff pressure stabilizer, which includes (a) a stabilizer port, which is configured to be coupled in fluid communication with the inflation lumen proximal port, (b) a substantially rigid protective housing, and (c) an elastic balloon, which is in fluid communication with the stabilizer port, and which is arranged such that an inflatable portion of the balloon is disposed inside the protective housing; and coupling the stabilizer port in fluid communication with the inflation lumen proximal port of the airway ventilation device, wherein the protective housing is shaped and the inflatable portion of the balloon is configured such that:

when the inflatable portion of the balloon contains a base low-pressure volume of air, the inflatable portion of the balloon has a base low pressure of 10 cm H2O, when the inflatable portion of the balloon contains a first medium-pressure volume of air, (a) the inflatable portion of the balloon has a first medium pressure of 25 cm H2O, and (b) none of or less than 10% of an outer surface of the inflatable portion of the balloon touches an inner surface of the protective housing, wherein the first medium-pressure volume of air equals the sum of (a) the base low-pressure volume of air and (b) a first incremental quantity of air of less than 10 cc, and when the inflatable portion of the balloon contains a second medium-pressure volume of air, (a) the inflatable portion of the balloon has a second medium pressure of 40 cm H2O, and (b) at least 20% of the outer surface of the inflatable portion of the balloon touches a portion of the inner surface of the protective housing, wherein the second medium-pressure volume of air equals the sum of (a) the base low-pressure volume of air and (b) a second incremental quantity of air that is between 10 cc and 60 cc.

There is additionally provided, in accordance with an Inventive concept 77 of the present invention, a method for use with an airway ventilation device having an inflatable cuff, an inflation lumen, and an inflation lumen proximal port, the method including:

providing a cuff pressure stabilizer, which includes (a) a stabilizer port, which is configured to be coupled in fluid communication with the inflation lumen proximal port, (b) a substantially rigid protective housing, and (c) an elastic balloon, which is in fluid communication with the stabilizer port, and which is arranged such that an inflatable portion of the balloon is disposed inside the protective housing; and coupling the stabilizer port in fluid communication with the inflation lumen proximal port of the airway ventilation device, wherein the protective housing is shaped and the inflatable portion of the balloon is configured such that:

when the inflatable portion of the balloon contains a base low-pressure volume of air, the inflatable portion of the balloon has a base low pressure of 10 cm H2O, the inflatable portion of the balloon is characterized by a pressure-volume curve that represents the pressure in the inflatable portion of the balloon when inflated with different incremental volumes of air beyond the base low-pressure volume of air, and the pressure-volume curve includes a rising point of inflection at a pressure of between 25 and 40 cm H2O.

There is additionally provided, in accordance with an Inventive concept 78 of the present invention, a method for use with an airway ventilation device having an inflatable cuff, an inflation lumen, and an inflation lumen proximal port, the method including:

providing a cuff pressure stabilizer, which includes (a) a stabilizer port, which is configured to be coupled in fluid communication with the inflation lumen proximal port, (b) a substantially rigid protective housing, which is shaped so as to define an inner surface that includes a frustoconical portion, and (c) an elastic balloon, which is in fluid communication with the stabilizer port, and which is arranged such that an inflatable portion of the balloon is disposed inside the protective housing, such that (i) none or less than 10% of an outer surface of the inflatable portion of the balloon touches the frustoconical portion when the inflatable portion of the balloon is inflated to a first medium pressure of 25 cm H2O, and (ii) at least 20% of the outer surface of the inflatable portion of the balloon touches at least a portion of the frustoconical portion when the inflatable portion of the balloon is inflated to a second medium pressure greater than the first medium pressure; and coupling the stabilizer port in fluid communication with the inflation lumen proximal port of the airway ventilation device.

The present invention will be more fully understood from the following detailed description of embodiments thereof, taken together with the drawings, in which:

BRIEF DESCRIPTION OF THE DRAWINGS

FIG. 4 includes a pressure-volume curve, in accordance with an application of the present invention.

DETAILED DESCRIPTION OF APPLICATIONS

Figure 1A:
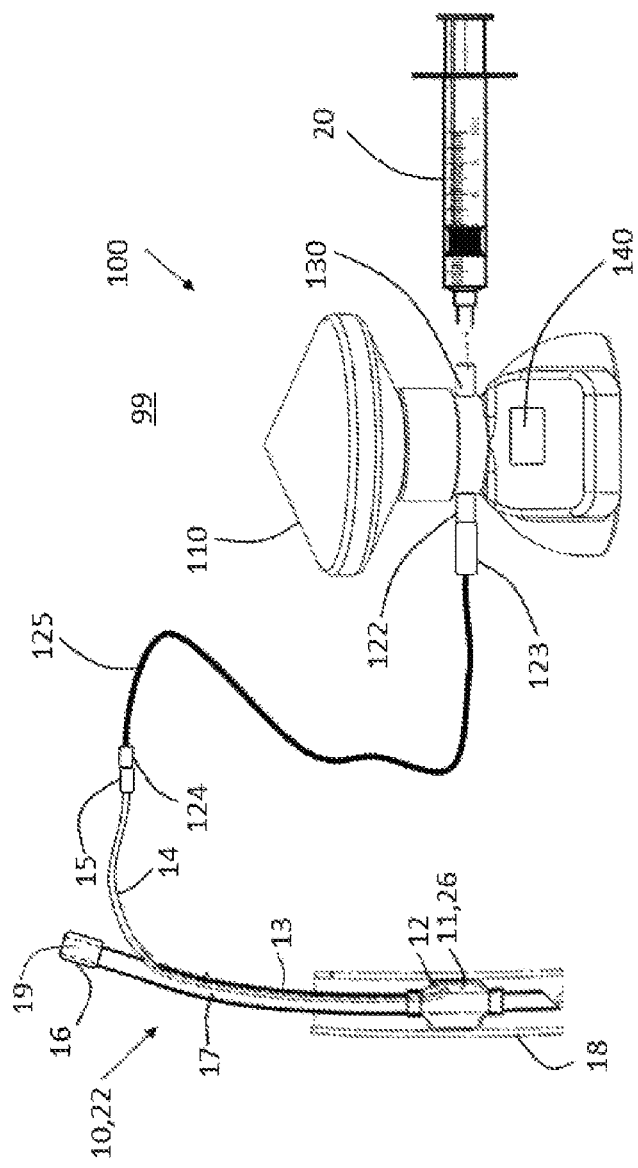
FIGS. 1A-C are schematic illustrations of a cuff pressure stabilizer for use with an airway ventilation device, in accordance with respective applications of the present invention.
Figure 1B:
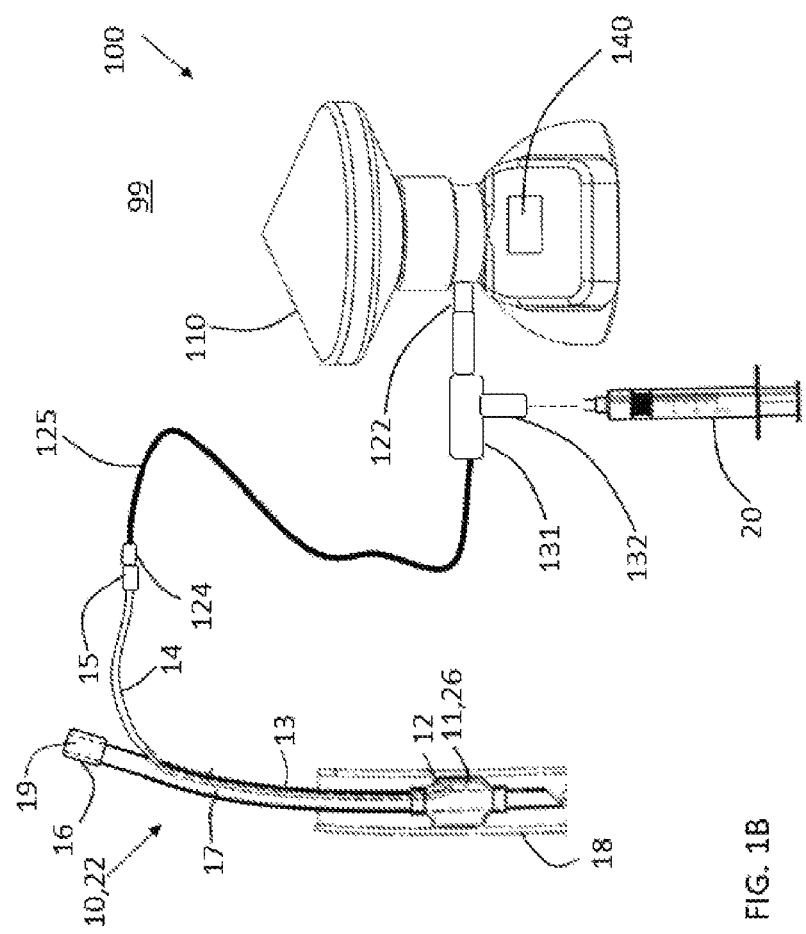
Figure 1C:
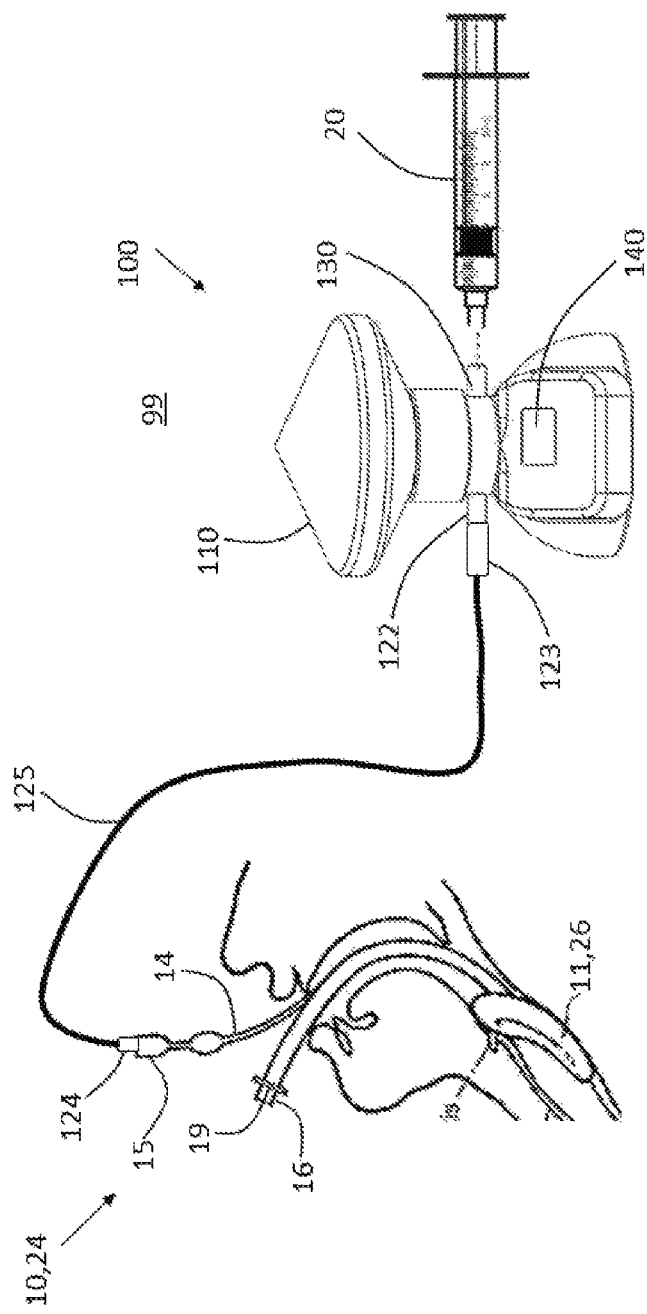

FIGS. 1A-C are schematic illustrations of a cuff pressure stabilizer 100 for use with an airway ventilation device 10, in accordance with respective applications of the present invention. For example, airway ventilation device 10 may be a tracheal ventilation tube 22, such as shown in FIG. 1A-B, or a laryngeal mask airway (LMA) device 24, such as shown in FIG. 1C. Cuff pressure stabilizer 100 is for use in contact with the atmosphere 99 (i.e., ambient air) of the Earth.

FIGS. 1A-C also show (a) airway ventilation device 10, which is not a component of cuff pressure stabilizer 100, (b) an external inflation source 20, such as a syringe, which is typically not a component of cuff pressure stabilizer 100, and (c) one or more connector tubes, described hereinbelow, which are optionally a component of cuff pressure stabilizer 100 (and may be removably or permanently coupled to cuff pressure stabilizer 100). Cuff pressure stabilizer 100 typically comprises a stabilizer port 122, which is in fluid communication with elastic balloon 148, described hereinbelow with reference to FIGS. 2A-B, and is configured to be coupled to the one or more connector tubes. The one or more connector tubes typically comprise a connector tube 125, which comprises an inflation lumen proximal port connector 124 that is shaped to form an air-tight seal with inflation lumen proximal port 15 of airway ventilation device 10, described immediately below. For some applications, inflation lumen proximal port connector 124 comprises a male conical fitting with a taper. For some applications, the taper is at least a 5% taper. For some applications, the taper is a 6% taper, and the male conical fitting with the 6% taper complies with International Standard ISO 594-1:1986, which is the standard for connections to conventional inflation lumen proximal ports of tracheal ventilation tubes and LMA masks.

Airway ventilation device 10 comprises an inflatable cuff 11, an inflation lumen 13, and an inflation lumen proximal port 15. Inflatable cuff 11 may comprise, for example, a balloon. Airway ventilation device 10 typically further comprises a cuff inflation lumen distal port 12, an airway ventilation tube ventilation port 16, an airway ventilation tube ventilation lumen 17, and an airway ventilation tube ventilator connection 19. For some applications, airway ventilation device 10 further comprises an inflating tube 14, which couples inflation lumen 13 in fluid communication with inflation lumen proximal port 15.

Reference is made to FIGS. 1A-B. In these configurations, airway ventilation device 10 is a tracheal ventilation tube 22, and inflatable cuff 11 is an inflatable cuff 26 mounted on tracheal ventilation tube 22, typically near a distal end of the tracheal ventilation tube, e.g., within 3 cm, such as within 1 cm, of the distal end. In these configurations, inflatable cuff 26 typically comprises a nearly non-compliant material, and/or typically has a volume of between 5 and 20 cc, depending on the size of airway ventilation device 10. Tracheal ventilation tube 22 is schematically shown inserted into a trachea 18, and inflatable cuff 26 is inflatable into sealing contact with the inner surface of trachea 18. As used in the present application, including in the claims, a "tracheal ventilation tube" comprises an endrotracheal tube (ETT) or a tracheotomy tube.

Reference is made to FIG. 1C. In this configuration, airway ventilation device 10 is a laryngeal mask airway (LMA) device 24, and inflatable cuff 11 is an inflatable cuff 28 (which is typically annular) that is insertable through a mouth of a patient to an inserted location within the patient, such that an anterior side of the cuff forms a seal around a laryngeal inlet of the patient upon inflation of the cuff. When cuff 28 is inflated to a working medium pressure, the LMA device is suitable for facilitating lung ventilation. For example, the working medium pressure may be between 15 and 60 cm H2O, such as between 20 and 60 cm H2O, e.g., between 25 and 55 cm H2O, such as between 40 and 50 cm H2O. In this configuration, inflatable cuff 28 typically has a volume of between 25 and 50 cc, depending on the size of LMA device 24.

Reference is made to FIGS. 1A and 1C. In these configurations, cuff pressure stabilizer 100 further comprises an inflation inlet port 130, which is in fluid communication with elastic balloon 148, described hereinbelow with reference to FIGS. 2A-B. Inflation inlet port 130 is configured to be coupled in fluid communication with external inflation source 20. In these configurations, connector tube 125 typically further comprises a stabilizer-port connector 123, which is configured to be coupled in fluid communication with stabilizer port 122.

Reference is made to FIG. 1B. In this configuration, cuff pressure stabilizer 100 further comprises an inlet junction 131, which couples in fluid communication connector tube 125, an inflation inlet port 132, first connector tube 133, and stabilizer port 122. Inflation inlet port 132 is configured to be coupled in fluid communication with external inflation source 20. In this configuration, cuff pressure stabilizer 100 typically does not comprise inflation inlet port 130, described hereinabove with reference to FIGS. 1A and 1C. Alternatively, inlet junction 131 is provided, but is not a component of cuff pressure stabilizer 100. In an alternative configuration (not shown), the configuration described with reference to FIG. 1B is combined with LMA device 24, described with reference to in FIG. 1C, mutatis mutandis.

Figure 2B:
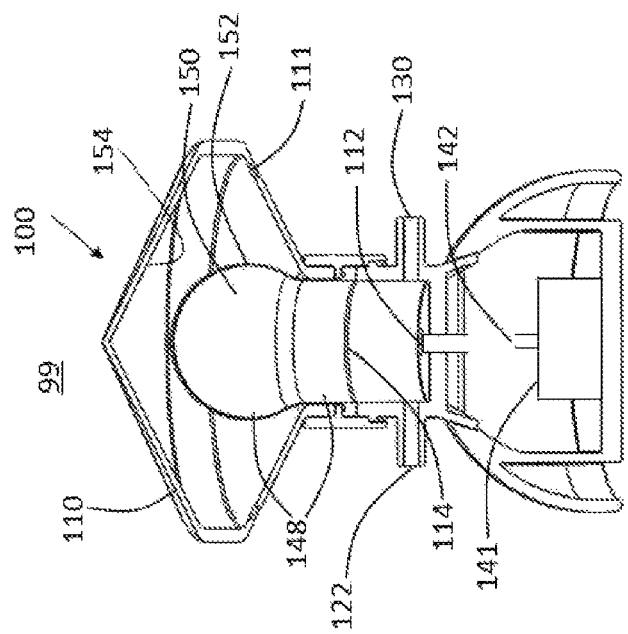
FIGS. 2A-B are additional schematic illustrations of the cuff pressure stabilizer of FIG. 1A, in accordance with an application of the present invention.
Figure 2A:
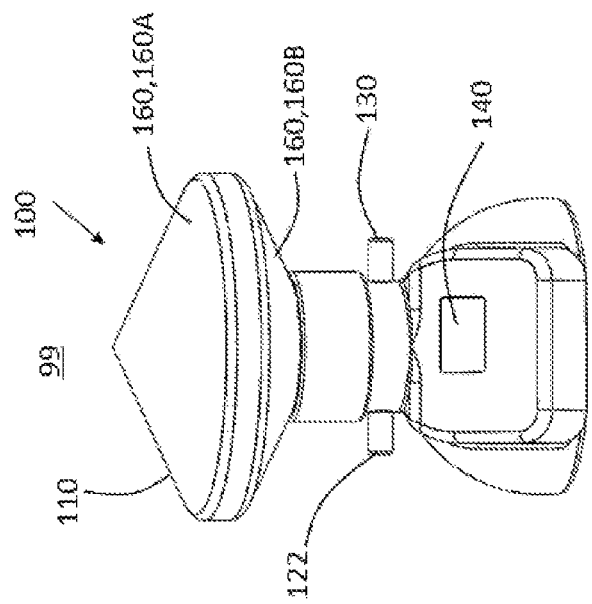

Reference is still made to FIGS. 1A-C, and is additionally made to FIGS. 2A-B, which are additional schematic illustrations of cuff pressure stabilizer 100, in accordance with an application of the present invention. FIG. 2B is a cross-section of FIG. 2A. FIGS. 2A-B show the configuration of cuff pressure stabilizer 100 shown in FIG. 1A.

Cuff pressure stabilizer 100 comprises:
- stabilizer port 122, described hereinabove, which is configured to be coupled in fluid communication with inflation lumen proximal port 15 of airway ventilation device 10;
- a substantially rigid protective housing 110; and
- an elastic balloon 148, which is in fluid communication with stabilizer port 122, and which is arranged such that an inflatable portion 150 of balloon 148 is disposed inside protective housing 110 (balloon 148 may include other portions, such as the neck thereof, that are not inflatable because they are constrained from inflating, e.g., by the casing of cuff pressure stabilizer 100).

As used in the present application, including in the claims, "substantially rigid," when referring to protective housing 110, means that the protective housing, when disposed in atmosphere 99, does not materially deform at least when the pressure in balloon 148 is between 0 and 120 cm H2O. i.e., the volume of protective housing 110 does not change by more than 10/when the pressure in the balloon increases from 0 cm H2O to 120 H2O.

Balloon 148 is shaped so as to define an inflation inlet 114, such as shown in FIG. 2B, and a proximal surface of protective housing 110 is typically shaped so as to define an inflation opening 112 aligned with inflation inlet 114, such that inflatable portion 150 of balloon 148 is inflatable via inflation opening 112 of protective housing 110.

Figures 3A, 3B, 3C, 3D:
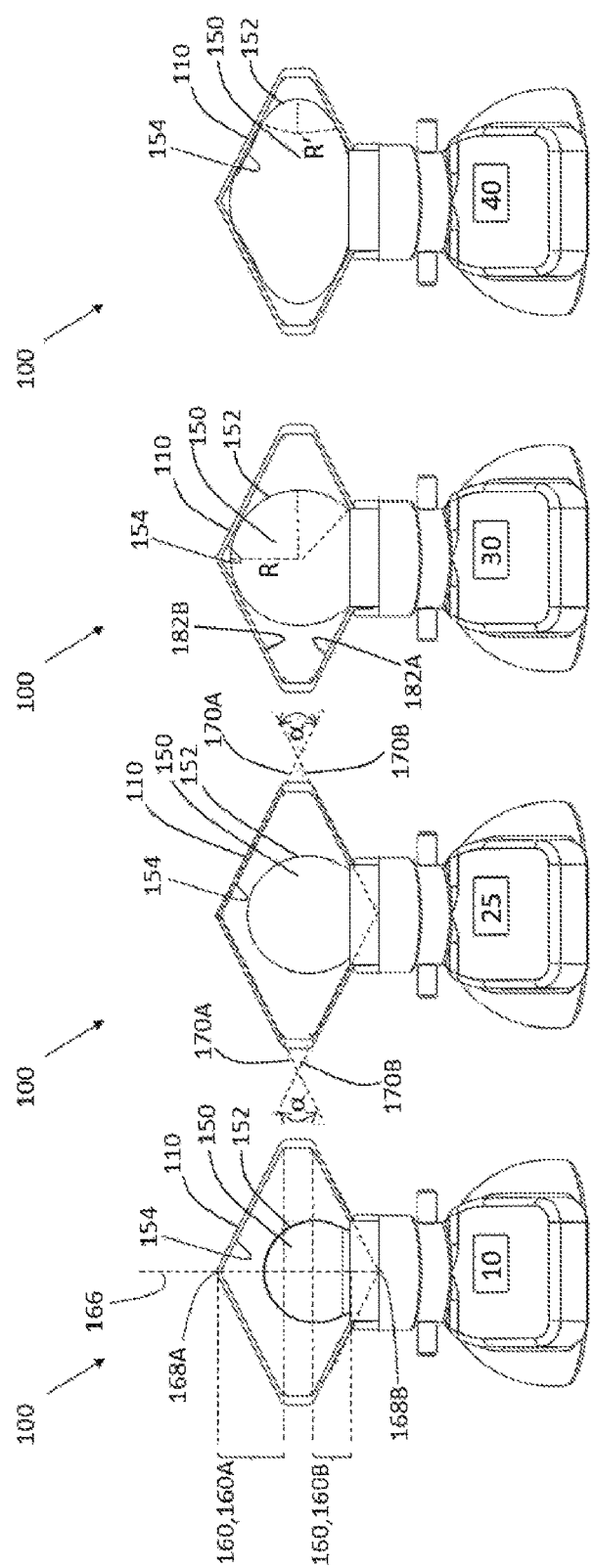
FIGS. 3A-D are schematic illustrations of the cuff pressure stabilizer of FIG. 1A with an inflatable portion of a balloon thereof inflated with different respective volumes, in accordance with an application of the present invention.

Reference is still made to FIGS. 1A-C and 2A-B, and is additionally made to FIGS. 3A-D, which are schematic illustrations of cuff pressure stabilizer 100 with inflatable portion 150 of balloon 148 inflated with different respective volumes, in accordance with an application of the present invention. FIGS. 3A-D show the configuration of cuff pressure stabilizer 100 shown in FIG. 1A. For some applications, protective housing 110 is shaped and inflatable portion 150 of balloon 148 is configured such that:

when inflatable portion 150 of balloon 148 contains a base low-pressure volume $V_B$ of air, inflatable portion 150 of balloon 148 has a base low pressure of 10 cm H2O, such as schematically illustrated in FIG. 3A, when inflatable portion 150 of balloon 148 contains a first medium-pressure volume $V_1$ of air, (a) inflatable portion 150 of balloon 148 has a first medium pressure of 25 cm H2O, and (b) none of or less than 10% of an outer surface 152 of inflatable portion 150 of balloon 148 touches (i.e., comes in direct physical contact with) an inner surface 154 of protective housing 110, such as schematically illustrated in FIG. 3B; the first medium-pressure volume $V_1$ of air equals the sum of (a) the base low-pressure volume $V_B$ of air and (b) a first incremental quantity $Q_1$ of air of less than 10 cc, and when inflatable portion 150 of balloon 148 contains a second medium-pressure volume $V_2$ of air, (a) inflatable portion 150 of balloon 148 has a second medium pressure of 40 cm H2O. and (b) at least 20% of outer surface 152 of inflatable portion 150 of balloon 148 touches a portion of inner surface 154 of protective housing 110, such as schematically illustrated in FIG. 3D; the second medium-pressure volume $V_2$ of air equals the sum of (a) the base low-pressure volume $V_B$ of air and (b) a second incremental quantity $Q_2$ of air that is between 10 cc and 60 cc, e.g., between 10 and 40 cc, such as between 10 and 30 cc.

FIG. 3C schematically illustrates inflatable portion 150 of balloon 148 containing another medium-pressure volume of air (greater than first medium-pressure volume $V_1$ and less than second medium-pressure volume $V_2$), such that inflatable portion 150 of balloon 148 has a medium pressure of 30 cm H2O, and less than 10% of an outer surface 152 of inflatable portion 150 of balloon 148 touches inner surface 154 of protective housing 110.

For example, the above-mentioned base low-pressure volume $V_B$ of air may be at least 2 cc, no more than 6 cc, and/or between 2 and 6 cc. For example, the above-mentioned first incremental quantity $Q_1$ of air may be at least 2 cc, no more than 10 cc (e.g., no more than 7 cc), and/or between 2 and 10 cc, such as between 2 and 7 cc. For example, the above-mentioned second medium incremental quantity $Q_2$ of air may be at least 10 cc (e.g., at least 20 cc), no more than 50 cc (e.g., no more than 40 cc), and/or between 10 and 50 cc, such as between 20 and 40 cc.

Alternatively or additionally, for some applications, protective housing 110 is shaped and inflatable portion 150 of balloon 148 is configured such that:

when inflatable portion 150 of balloon 148 contains a base low-pressure volume $V_B$ of air, inflatable portion 150 of balloon 148 has a base low pressure of 10 cm H2O, such as schematically illustrated in FIG. 3A, when inflatable portion 150 of balloon 148 contains a first medium-pressure volume $V_1$ of air, (a) inflatable portion 150 of balloon 148 has a first medium pressure of 25 cm H2O, and (b) none of or less than 10% of an outer surface 152 of inflatable portion 150 of balloon 148 touches (i.e., comes in direct physical contact with) an inner surface 154 of protective housing 110, such as schematically illustrated in FIG. 3B; the first medium-pressure volume $V_1$ of air equals the sum of (a) the base low-pressure volume $V_B$ of air and (b) a first incremental quantity of air, typically less than 10 cc, and when inflatable portion 150 of balloon 148 contains a second medium-pressure volume $V_2$ of air, (a) inflatable portion 150 of balloon 148 has a second medium pressure, and (b) at least 20% of outer surface 152 of inflatable portion 150 of balloon 148 touches a portion of inner surface 154 of protective housing 110, such as schematically illustrated in FIG. 3D; the second medium-pressure volume $V_2$ of air equals the sum of (a) the base low-pressure volume $V_B$ of air and (b) a second incremental quantity of air that is between 1.1 and 3 times the first incremental quantity of air.

Protective housing 110 is shaped so as to define at least one opening 111 therethrough to the atmosphere 99, in order to maintain air pressure within protective housing 110 but outside balloon 148 at approximately atmospheric pressure. For some applications, protective housing 110 has a volume of at least 20 cc (e.g., at least 30 cc), no more than 80 cc (e.g., no more than 60 cc), and/or between 20 and 80 cc, such as between 30 and 60 cc.

Reference is again made to FIGS. 2A-B and 3A-D. For some applications, inner surface 154 of substantially rigid protective housing 110 is shaped so as to include a frustoconical portion 160 (labeled in FIGS. 2A and 3A). Balloon 148 is arranged such that inflatable portion 150 of balloon 148 is disposed inside protective housing 110, typically such that:

none or less than 10% of outer surface 152 of inflatable portion 150 of balloon 148 touches frustoconical portion 160 when inflatable portion 150 of balloon 148 is inflated to a first medium pressure of 25 cm H2O, such as schematically illustrated in FIG. 3B, and at least 20% of outer surface 152 of inflatable portion 150 of balloon 148 touches at least a portion of frustoconical portion 160 when inflatable portion 150 of balloon 148 is inflated to a second medium pressure greater than the first medium pressure, such as schematically illustrated in FIG. 3D.

For some applications, frustoconical portion 160 of inner surface 154 of protective housing 110 that comes into contact with balloon 148 when balloon 148 is inflated to a medium pressure of 50 cm H2O has an area of at least 10 cm2, no more than 60 cm2, and/or between 10 and 60 cm2. For some applications, protective housing 110 is cylindrically symmetric about a central longitudinal axis 166 defined by frustoconical portion 160.

For some applications, frustoconical portion 160 is a first frustoconical portion 160A, and protective housing 110 is shaped such that inner surface 154 includes a second frustoconical portion 160B. First and second frustoconical portions 160A and 160B geometrically define different respective apices 168A and 168B. (It is to be understood that for a frustoconical portion that is not conical, the apex is the geometric apex of the portion of the cone cut off to produce the frustum that defines the frustoconical portion.) Optionally, first and second frustoconical portions 160A and 160B share a common central longitudinal axis 166, such as shown. Alternatively, first and second frustoconical portions 160A and 160B do not share a common central longitudinal axis (configuration not shown).

First and second frustoconical portions 160A and 160B geometrically define respective cones 170A and 170B (portions of which are labeled in FIG. 3B). For some applications, cones 170A and 170B intersect each other at one or more angles α (alpha), at least one of which is greater than 45 degrees. Typically, at least one of the angles is less than 90 degrees. For some applications, all of the angles are greater than 45 degrees, and/or all of the angles are less than 90 degrees. For applications in which first and second frustoconical portions 160A and 160B share common central longitudinal axis 166, such as shown, the respective cones 170A and 170B geometrically defined by first and second frustoconical portions 160A and 160B intersect each other at exactly one angle α (alpha). As used in the present application, including in the claims, "geometrically defined" means that the shape is defined abstractly in geometry, but not necessarily as a structural element of the device; for example, cones 170A and 170B are not necessarily structural elements of protective housing 110, although they could be. As used in the present application, including in the claims, the angle between two geometrical shapes is the smaller of the two supplementary angles between the two geometrical shapes, or equals 90 degrees if the two geometrical shapes are perpendicular.

For some applications, balloon 148 is arranged such that inflatable portion 150 of balloon 148 is disposed inside protective housing 110 such that as inflatable portion 150 of balloon 148 is inflated from the first medium pressure toward the second medium pressure, outer surface 152 of inflatable portion 150 of balloon 148 increases contact with second frustoconical portion 160B before increasing contact with first frustoconical portion 160A.

For some applications, protective housing 110 is shaped such that frustoconical portion 160 is part of a conical portion of inner surface 154. For example, first frustoconical portion 160A is illustrated as part of a conical portion of inner surface 154.

For some applications, inner surface 154 of protective housing 110 includes a proximal portion 182A that faces generally distally, and a distal portion 182B that faces generally proximally toward proximal portion 182A (labeled in FIG. 3C). One of proximal and distal portions 182A and 182B of inner surface 154 includes frustoconical portion 160. For some applications, a cone geometrically defined by frustoconical portion 160 intersects the other one of proximal and distal portions 182A and 182B of inner surface 154 at one or more angles, at least one of which is greater than 45 degrees.

For some applications, the other one of proximal and distal portions 182A and 182B of inner surface 154 is generally flat (configuration not shown). Frustoconical portion 160 geometrically defines a cone, which, for some of these applications, intersects the other one of proximal and distal portions 182A and 182B of inner surface 154 at one or more angles, e.g., at exactly one angle. At least one (e.g., all) of the one or more angles is greater than 45 degrees.

For some applications, frustoconical portion 160 is a first frustoconical portion 160A, and the other one of proximal and distal portions 182A and 182B of inner surface 154 defines a second frustoconical portion 160B. For some of these applications, respective cones geometrically defined by first and second frustoconical portions 160A and 160B intersect each other at one or more angles, e.g., at exactly one angle. At least one (e.g., all) of the one or more angles is greater than 45 degrees.

Reference is made to FIGS. 1A-C, 2A-B, and 3A-D. For some applications, cuff pressure stabilizer 100 further comprises an electronic pressure measurement circuit 141, comprising a sensor (labeled in FIG. 2B), which is configured to sense a pressure in inflatable portion 150 of balloon 148 (e.g., via an air inlet 142 for fluid communication between the pressure sensor and the balloon). The pressure sensor is disposed in balloon 148 or in a volume that is in fluid communication with balloon 148. Cuff pressure stabilizer 100 further comprises a pressure display 140, which is configured to display the pressure sensed by the pressure sensor. Pressure display 140 may be digital or analog. It is noted that the pressure sensor and pressure display 140 only sense and display the pressure, respectively, but are not involved in setting or otherwise regulating the pressure in balloon 148 or inflatable cuff 11; in other words, the cuff pressure stabilizer 100 automatically mechanically and non-electrically stabilizes the pressure in inflatable cuff 11.

Electronic pressure measurement circuit 141 and display 140 comprise: a pressure sensor, a battery power supply, an electronic controller, a turn-ON switch, and display 140. For some applications, electronic pressure measurement circuit 141 takes a pressure measurement at time intervals greater than 10 seconds and less than 5 minutes (such as once per 30 seconds, or once per 60 seconds). For some applications, the battery drains within less than 30 days of use (such as less than 14 days, or less than 7 days). This feature ensures the disposability of the device within the intended time limit of single-patient residence in hospital intensive care. For some applications, the turn-ON switch cannot be turned off to stop the battery drain after initial turn-ON.

Reference is now made to FIG. 4, which includes a pressure-volume curve 200, in accordance with an application of the present invention. FIG. 4 also includes a known pressure-volume curve 202, measured in an experiment conducted on behalf of the inventors using the TRACOE® smart Cuff Manager (TRACOE medical GmbH, Nieder-Olm, Germany), which was similar to the pressure-equalizing device described in the above-mentioned US Patent Application Publication 2015/0283343 to Schnell et al. Inflatable portion 150 of balloon 148 of cuff pressure stabilizer 100 is characterized by pressure-volume curve 200, which represents the pressure in inflatable portion 150 of balloon 148 when inflated with different incremental volumes of air ($\Delta V$) beyond the base low-pressure volume $V_B$ of air corresponding to the base low pressure of 10 cm H2O described hereinabove with reference to FIGS. 3A-B. Pressure-volume curve 200 illustrated in FIG. 4 is an exemplary pressure-volume curve; a large number of additional pressure-volume curves having the general properties of pressure-volume curve 200 are possible, and are within the scope of the present invention.

For some applications, such as shown in FIG. 4, pressure-volume curve 200 does not include a local maximum pressure at any pressure between 20 and 50 cm H2O. By contrast, known pressure-volume curve 202 includes a local maximum pressure at about 31 cm H2O (at about 10 cc of incremental air). Alternatively, for other applications (not shown), pressure-volume curve 200 includes a local maximum pressure and a local minimum pressure at a greater incremental volume than the local maximum pressure, and (a) a pressure difference between the local maximum pressure and the local minimum pressure is less than 3 cm H2O, e.g., less than 2 cm H2O, and/or (b) a volume difference between the local maximum pressure and the local minimum pressure is less than 40 cc. e.g., less than 30 cc.

For some applications, an average rate of change of pressure-volume curve 200 over a first pressure interval 210 between 40 and 50 cm H2O is between 0.5 and 3 cm H2O/cc, such as between 0.5 and 2 cm H2O/cc, e.g., between 0.5 and 1 cm H2O/cc. By contrast, an average rate of change of known pressure-volume curve 202 over first pressure interval 210 is about 4 cm H2O/cc. Alternatively or additionally, for some applications, an average rate of change of pressure-volume curve 200 over a second pressure interval 212 between 50 and 60 cm H2O is between 0.5 and 3 cm H2O/cc, such as between 0.5 and 2 cm H2O/cc, e.g., between 0.5 and 1 cm H2O/cc. By contrast, an average rate of change of known pressure-volume curve 202 over second pressure interval 212 is about 6 cm H2O/cc. As is known in the mathematical arts, the "average rate of change" is the slope of the secant line joining respective points on the curve at the endpoints of the relevant interval.

Providing these relatively low average rates of change has the effect of stabilizing the pressure in inflatable cuff 28 of LMA device 24. Relatively small increases or decreases in the volume of inflatable cuff 28, for example caused by movement of cuff 28 against the patient's laryngeal inlet, result in corresponding decreases or increases in the volume of inflatable portion 150 of balloon 148. In the relevant typically desired pressure range of LMA cuffs of between 40 and 60 cm H2O, these changes in the volume of inflatable portion 150 have only minimal effect on the pressure in inflatable portion 150, and thus in inflatable cuff 28, because of the elasticity of balloon 148.

Alternatively or additionally, for some applications, an average rate of change of pressure-volume curve 200 over a pressure interval 214 between 20 and 30 cm H2O is between 1 and 5 cm H2O/cc, such as between 1 and 4 cm H2O/cc, e.g., between 1 and 3 cm H2O/cc. Providing these relatively low average rates of change has the effect of stabilizing the pressure in inflatable cuff 26 of tracheal ventilation tube 22. Relatively small increases or decreases in the volume of inflatable cuff 26, for example caused by movement of cuff 26 in trachea 18, result in corresponding decreases or increases in the volume of inflatable portion 150 of balloon 148. In the relevant typically desired pressure range of tracheal ventilation tube cuffs of between 20 and 30 cm H2O, these changes in the volume of inflatable portion 150 have only minimal effect on the pressure in inflatable portion 150, and thus in inflatable cuff 26, because of the elasticity of balloon 148.

Further alternatively or additionally, for some applications, pressure-volume curve 200 includes a rising point of inflection 220 at a pressure of between 25 and 40 cm H2O and/or at an incremental volume between 5 and 60 cc, such as between 10 and 30 cc. For these applications, pressure-volume curve 200 typically does not include a local maximum pressure at any pressure between 20 and 50 cm H2O. By contrast, known pressure-volume curve 202 does not include a rising point of inflection, and does include local maximum and minimum pressures. As is known in the mathematical arts, a "rising point of inflection" is a point of inflection at which the third derivative is positive, i.e., the curve is upward-flowing about the point.

Although cuff pressure stabilizer 100 has been described as being used with inflatable cuff 11 of airway ventilation device 10, cuff pressure stabilizer 100 may alternatively be used with other inflatable chambers of other medical devices or non-medical devices. For example, the inflatable chamber may be a Foley catheter balloon, a gastric balloon, a balloon of colonoscope, or a balloon of an endoscope.

In the description and claims of the present application, each of the verbs, "comprise," "include" and "have," and conjugates thereof, are used to indicate that the object or objects of the verb are not necessarily a complete listing of members, components, elements or parts of the subject or subjects of the verb. The articles "a" and "an" are used herein to refer to one or to more than one (i.e., to at least one) of the grammatical object of the article. By way of example, "an element" means one element or more than one element. The term "including" is used herein to mean, and is used interchangeably with, the phrase "including but not limited to." The term "or" is used herein to mean, and is used interchangeably with, the term "and/or," unless context clearly indicates otherwise. The term "such as" is used herein to mean, and is used interchangeably with, the phrase "such as but not limited to."

All publications, patent applications, patents, and other references mentioned herein are incorporated by reference in their entirety. In case of conflict, the present patent specification, including definitions, will prevail. In addition, the materials, methods, and examples are illustrative only and not intended to be limiting.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A cuff pressure stabilizer for use with an airway ventilation device having an inflatable cuff, an inflation lumen, and an inflation lumen proximal port, the cuff pressure stabilizer comprising:
   a stabilizer port, which is configured to be coupled in fluid communication with the inflation lumen proximal port;
   a substantially rigid protective housing; and
   an elastic balloon, which is in fluid communication with the stabilizer port, and which is arranged such that an inflatable portion of the balloon is disposed inside the protective housing,
   wherein the protective housing is shaped and the inflatable portion of the balloon is configured such that:
   when the inflatable portion of the balloon contains a base low-pressure volume of air, the inflatable portion of the balloon has a base low pressure of 10 cm $H_2O$,
   when the inflatable portion of the balloon contains a first-medium-pressure volume of air, (a) the inflatable portion of the balloon has a first-medium pressure of 25 cm $H_2O$, and (b) none of or less than 10% of an outer surface of the inflatable portion of the balloon touches an inner surface of the protective housing, wherein the first-medium-pressure volume of air equals the sum of (a) the base low-pressure volume of air and (b) a first incremental quantity of air of less than 10 cc, and
   when the inflatable portion of the balloon contains a second-medium-pressure volume of air, (a) the inflatable portion of the balloon has a second-medium pressure of 40 cm $H_2O$, and (b) at least 20% of the outer surface of the inflatable portion of the balloon touches a portion of the inner surface of the protective housing, wherein the second-medium-pressure volume of air equals the sum of (a) the base low-pressure volume of air and (b) a second incremental quantity of air that is between 10 cc and 60 cc, wherein the protective housing is shaped so as to define an inner surface that includes a frustoconical portion, and wherein the protective housing is shaped and the inflatable portion of the balloon is configured such that:

when the inflatable portion of the balloon contains the first-medium-pressure volume of air, none or less than 10% of the outer surface of the inflatable portion of the balloon touches the frustoconical portion, and when the inflatable portion of the balloon contains the second-medium-pressure volume of air, at least 20% of the outer surface of the inflatable portion of the balloon touches at least a portion of the frustoconical portion.

2. The cuff pressure stabilizer according to claim 1, wherein the second incremental quantity of air is less than 40 cc.

3. The cuff pressure stabilizer according to claim 2, wherein the second incremental quantity of air is less than 30 cc.

4. The cuff pressure stabilizer according to claim 1,
wherein the inflatable portion of the balloon is characterized by a pressure-volume curve that represents the pressure in the inflatable portion of the balloon when inflated with different incremental volumes of air beyond the base low-pressure volume of air, and
wherein the pressure-volume curve does not include a local maximum pressure at any pressure between 20 and 50 cm $H_2O$.

5. The cuff pressure stabilizer according to claim 1,
wherein the inflatable portion of the balloon is characterized by a pressure-volume curve that represents the pressure in the inflatable portion of the balloon when inflated with different incremental volumes of air beyond the base low-pressure volume of air,
wherein the pressure-volume curve includes a local maximum pressure and a local minimum pressure at a greater incremental volume than the local maximum pressure, and
wherein a pressure difference between the local maximum pressure and the local minimum pressure is less than 3 cm $H_2O$.

6. The cuff pressure stabilizer according to claim 1,
wherein the inflatable portion of the balloon is characterized by a pressure-volume curve that represents the pressure in the inflatable portion of the balloon when inflated with different incremental volumes of air beyond the base low-pressure volume of air,
wherein the pressure-volume curve includes a local maximum pressure and a local minimum pressure at a greater incremental volume than the local maximum pressure, and
wherein a volume difference between the local maximum pressure and the local minimum pressure is less than 40 cc.

7. The cuff pressure stabilizer according to claim 1,
wherein the inflatable portion of the balloon is characterized by a pressure-volume curve that represents the pressure in the inflatable portion of the balloon when inflated with different incremental volumes of air beyond the base low-pressure volume of air, and
wherein an average rate of change of the pressure-volume curve over a pressure interval between 40 and 50 cm $H_2O$ is between 0.5 and 3 cm $H_2O$/cc.

8. A cuff pressure stabilizer for use with an airway ventilation device having an inflatable cuff, an inflation lumen, and an inflation lumen proximal port, the cuff pressure stabilizer comprising:

a stabilizer port, which is configured to be coupled in fluid communication with the inflation lumen proximal port;
a substantially rigid protective housing; and
an elastic balloon, which is in fluid communication with the stabilizer port, and which is arranged such that an inflatable portion of the balloon is disposed inside the protective housing,
wherein the protective housing is shaped and the inflatable portion of the balloon is configured such that:

when the inflatable portion of the balloon contains a base low-pressure volume of air, the inflatable portion of the balloon has a base low pressure of 10 cm $H_2O$, when the inflatable portion of the balloon contains a first-medium-pressure volume of air, none of or less than 10% of an outer surface of the inflatable portion of the balloon touches an inner surface of the protective housing, wherein the first-medium-pressure volume of air equals the sum of (a) the base low-pressure volume of air and (b) a first incremental quantity of air of less than 10 cc, and when the inflatable portion of the balloon contains a second-medium-pressure volume of air, (a) the inflatable portion of the balloon has a second-medium pressure of 40 cm $H_2O$, and (b) at least 20% of the outer surface of the inflatable portion of the balloon touches a portion of the inner surface of the protective housing, wherein the second-medium-pressure volume of air equals the sum of (a) the base low-pressure volume of air and (b) a second incremental quantity of air that is between 10 cc and 60 cc, wherein the inflatable portion of the balloon is characterized by a pressure-volume curve that represents the pressure in the inflatable portion of the balloon when inflated with different incremental volumes of air beyond the base low-pressure volume of air, and wherein an average rate of change of the pressure-volume curve over a pressure interval between 50 and 60 cm $H_2O$ is between 0.5 and 3 cm $H_2O$/cc.

9. The cuff pressure stabilizer according to claim 1,
wherein the inflatable portion of the balloon is characterized by a pressure-volume curve that represents the pressure in the inflatable portion of the balloon when inflated with different incremental volumes of air beyond the base low-pressure volume of air, and
wherein an average rate of change of the pressure-volume curve over a pressure interval between 20 and 30 cm $H_2O$ is between 1 and 5 cm $H_2O$/cc.

10. The cuff pressure stabilizer according to claim 1, wherein the frustoconical portion of the inner surface of the protective housing that comes into contact with the balloon when the balloon is inflated to a medium pressure of 50 cm $H_2O$ has an area of between 10 and 60 cm².

11. The cuff pressure stabilizer according to claim 1, wherein the protective housing is shaped such that the frustoconical portion is part of a conical portion of the inner surface.

12. The cuff pressure stabilizer according to claim 1, wherein the protective housing is cylindrically symmetric about a central longitudinal axis defined by the frustoconical portion.

13. The cuff pressure stabilizer according to claim 1, wherein the frustoconical portion is a first frustoconical portion, and wherein the protective housing is shaped such that the inner surface includes a second frustoconical portion, and wherein the first and the second frustoconical portions geometrically define different respective apices.

14. The cuff pressure stabilizer according to claim 13, wherein the first and the second frustoconical portions share a common central longitudinal axis.

15. The cuff pressure stabilizer according to claim 13, wherein respective cones geometrically defined by the first and the second frustoconical portions intersect each other at one or more angles, at least one of which is greater than 45 degrees.

16. The cuff pressure stabilizer according to claim 15, wherein the respective cones geometrically defined by the first and the second frustoconical portions intersect each other at exactly one angle.

17. The cuff pressure stabilizer according to claim 13, wherein the balloon is arranged such that the inflatable portion of the balloon is disposed inside the protective housing such that as the inflatable portion of the balloon is inflated from the first-medium pressure toward the second-medium pressure, the outer surface of the inflatable portion of the balloon increases contact with the second frustoconical portion before increasing contact with the first frustoconical portion.

18. The cuff pressure stabilizer according to claim 1,
wherein the balloon is shaped so as to define an inflation inlet, and wherein a proximal surface of the protective housing is shaped so as to define an inflation opening aligned with the inflation inlet, such that the inflatable portion of the balloon is inflatable via the inflation opening of the protective housing,
wherein the inner surface of the protective housing includes a proximal portion that faces generally distally, and a distal portion that faces generally proximally toward the proximal portion, and
wherein one of the proximal and the distal portions of the inner surface includes the frustoconical portion.

19. The cuff pressure stabilizer according to claim 18, wherein a cone geometrically defined by the frustoconical portion intersects the other one of the proximal and the distal portions of the inner surface at one or more angles, at least one of which is greater than 45 degrees.

20. The cuff pressure stabilizer according to claim 18, wherein the other one of the proximal and the distal portions of the inner surface is generally flat.

21. The cuff pressure stabilizer according to claim 20, wherein a cone geometrically defined by the frustoconical portion intersects the other one of the proximal and the distal portions of the inner surface at one or more angles, at least one of which is greater than 45 degrees.

22. The cuff pressure stabilizer according to claim 18, wherein the frustoconical portion is a first frustoconical portion, and wherein the other one of the proximal and the distal portions of the inner surface defines a second frustoconical portion.

23. A cuff pressure stabilizer for use with an airway ventilation device having an inflatable cuff, an inflation lumen, and an inflation lumen proximal port, the cuff pressure stabilizer comprising:
a stabilizer port, which is configured to be coupled in fluid communication with the inflation lumen proximal port;
a substantially rigid protective housing; and
an elastic balloon, which is in fluid communication with the stabilizer port, and which is arranged such that an inflatable portion of the balloon is disposed inside the protective housing,
wherein the protective housing is shaped and the inflatable portion of the balloon is configured such that:
when the inflatable portion of the balloon contains a base low-pressure volume of air, the inflatable portion of the balloon has a base low pressure of 10 cm $H_2O$,
when the inflatable portion of the balloon contains a first-medium-pressure volume of air, none of or less than 10% of an outer surface of the inflatable portion of the balloon touches an inner surface of the protective housing, wherein the first-medium-pressure volume of air equals the sum of (a) the base low-pressure volume of air and (b) a first incremental quantity of air of less than 10 cc, and
when the inflatable portion of the balloon contains a second-medium-pressure volume of air, (a) the inflatable portion of the balloon has a second-medium pressure of 40 cm $H_2O$, and (b) at least 20% of the outer surface of the inflatable portion of the balloon touches a portion of the inner surface of the protective housing, wherein the second-medium-pressure volume of air equals the sum of (a) the base low-pressure volume of air and (b) a second incremental quantity of air that is between 10 cc and 60 cc,
wherein the cuff pressure stabilizer further comprises:
a pressure sensor, which is configured to sense a pressure in the inflatable portion of the balloon; and
a pressure display, which is configured to display the pressure sensed by the pressure sensor.

24. A system comprising the cuff pressure stabilizer according to claim 1, wherein the system further comprises the airway ventilation device.

25. The system according to claim 24, wherein the airway ventilation device comprises a tracheal ventilation tube.

26. The system according to claim 24, wherein the airway ventilation device comprises a laryngeal mask airway (LMA) device.

* * * * *